(12) United States Patent  (10) Patent No.: US 7,597,445 B2
Sakurada et al.  (45) Date of Patent: Oct. 6, 2009

(54) PROGRAM FOR OPTOMETRY, RECORDING MEDIUM AND SUBJECTIVE OPTOMETRIC APPARATUS HAVING THE OPTOMETRIC PROGRAM, AND OPTOMETRIC METHOD

(75) Inventors: Tomohiro Sakurada, Tokyo (JP); Tatsuro Yokoi, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 161 days.

(21) Appl. No.: 11/726,067

(22) Filed: Mar. 21, 2007

(65) Prior Publication Data
US 2007/0229762 A1  Oct. 4, 2007

(30) Foreign Application Priority Data
Mar. 31, 2006  (JP) .............................. 2006-100239

(51) Int. Cl.
*A61B 3/02* (2006.01)
(52) U.S. Cl. ...................................... 351/243; 351/222
(58) Field of Classification Search ................. 359/243; 351/243
See application file for complete search history.

(56) References Cited

U.S. PATENT DOCUMENTS
6,048,064 A * 4/2000 Hosoi et al. .................. 351/212

FOREIGN PATENT DOCUMENTS
JP  2002-143092  5/2002

* cited by examiner

*Primary Examiner*—Jordan M. Schwartz
*Assistant Examiner*—James C Jones
(74) *Attorney, Agent, or Firm*—Chapman and Cutler LLP (57) ABSTRACT

The present invention is directed to a program for optometry, which is used for a control device. The program includes a first unit to measure an amount of heterophoria of eyes of an examinee to be examined in a horizontal heterophoria examination, a second unit to display an operating method to allow the examinee to implement a Sheard criterion identifying examination on a display device, a third unit to allow the examinee to implement a convergent or divergent test of the eyes based on the operating method, and a fourth unit to calculate a prism amount for prescriptions based on the heterophoria amount and the convergence or divergence of the eyes.

13 Claims, 6 Drawing Sheets

PROGRAM FOR OPTOMETRY, RECORDING MEDIUM AND SUBJECTIVE OPTOMETRIC APPARATUS HAVING THE OPTOMETRIC PROGRAM, AND OPTOMETRIC METHOD

CROSS-REFERENCE TO THE RELATED APPLICATION

This application is based on and claims priority from Japanese Patent Application No. 2006-100239, filed on Mar. 31, 2006, the disclosure of which is incorporated herein by reference in its entirety.

BACKGROUND OF THE INVENTION

1. Field of the Invention

The present invention relates to a program for optometry, a recording medium and a subjective optometric apparatus having the optometric program, and an optometric method.

2. Description of the Related Art

In general, a subjective optometric apparatus which has a main body provided with a pair of right and left optometric units which are disposed so as to be capable of adjusting an interval therebetween, and a target displaying device which is visibly recognized by an examinee via optometric windows of the optometric units is known (for example, see Japanese Patent Application Publication No. 2002-143092).

In the subjective optometric apparatus of this type, a plurality of test lenses, polarizing plates, and other optical devices to be selectively disposed on each of the optometric windows are provided in the optometric units. As one of such optical devices, for example, a rotary prism used to carry out a prism correction for heterophoria or heterotropia is known.

In performing the above-mentioned prism correction for heterophoria or heterotropia, generally an amount of heterophoria of the examinee is first determined. Next, a fusional force of the examinee is determined and the prism correction is performed if it is found out that the determined fusional force cannot adequately compensate the heterophoria amount of the examinee.

In this case, as criterion for identifying whether the fusional force can adequately compensate the heterophoria amount of the examinee, Sheard criterion and Percival criterion are widely known.

In the case of the Percival criterion, it is required that both of a convergence force and a divergence force of the examinee be measured regardless of whether an ocular deviation of the examinee has an inward or an outward direction. The examinee is burdened with these examinations since they take such a long time.

On the other hand, in the case of the Sheard criterion, it is required that the fusional divergence reserve of the examinee be measured if the ocular deviation of the examinee is in the inward direction, and the fusional convergence reserve of the examinee be measured if the ocular deviation is in the outward direction. Therefore, the examinations based on the Sheard criterion reduce the burden imposed on the examinee and allow a greater reduction in time in comparison with that of the Percival criterion.

However, a relationship among the heterophoria amount, an amount of the convergence or the divergence of the examinee, and values of the Sheard criterion are not always known by an examiner. In practice, these examinations are sometimes not performed and unsuitable values are prescribed.

Furthermore, although conventional system optometric devices allow a convergence or divergence test for identifying the criterion of Sheard or Percival to be performed, they have no function for calculating an amount of a prism suitable for a prescription based on the criterion values.

SUMMARY OF THE INVENTION

Therefore, an object of the present invention is to provide a program for optometry which allows an amount of a prism suitable for a prescription to be calculated based on an amount of heterophoria and an amount of convergence or divergence of the examinee, and a recording medium and a subjective optometric apparatus which have the optometric program.

To achieve the above object, the optometric program, the recording medium and the subjective optometric apparatus having the program according to the present invention operates a computer as a first unit to measure an amount of heterophoria of the eyes of an examinee to be examined in a horizontal heterophoria examination, a second unit to display an operating method on a display device to allow the examinee to implement a Sheard criterion identifying test, a third unit to allow the examinee to implement a convergent or divergent test of the eyes based on the operating method, and a fourth unit to calculate a prism amount for prescriptions based on the heterophoria amount and the convergence or divergence of the eyes.

According to the above structure, an operating device allows the heterophoria amount of the eyes of the examinee to be calculated and guides as to how to proceed with the examination of the convergence or divergence of the eyes so that an amount of a prism suitable for prescriptions is calculated based on the heterophoria amount and the amount of convergence or divergence of the eyes.

DETAILED DESCRIPTION OF THE PREFERRED EMBODIMENTS

Preferred embodiments of the present invention will be explained with reference to the accompanying drawings below.

[Structure]

Figure 1:
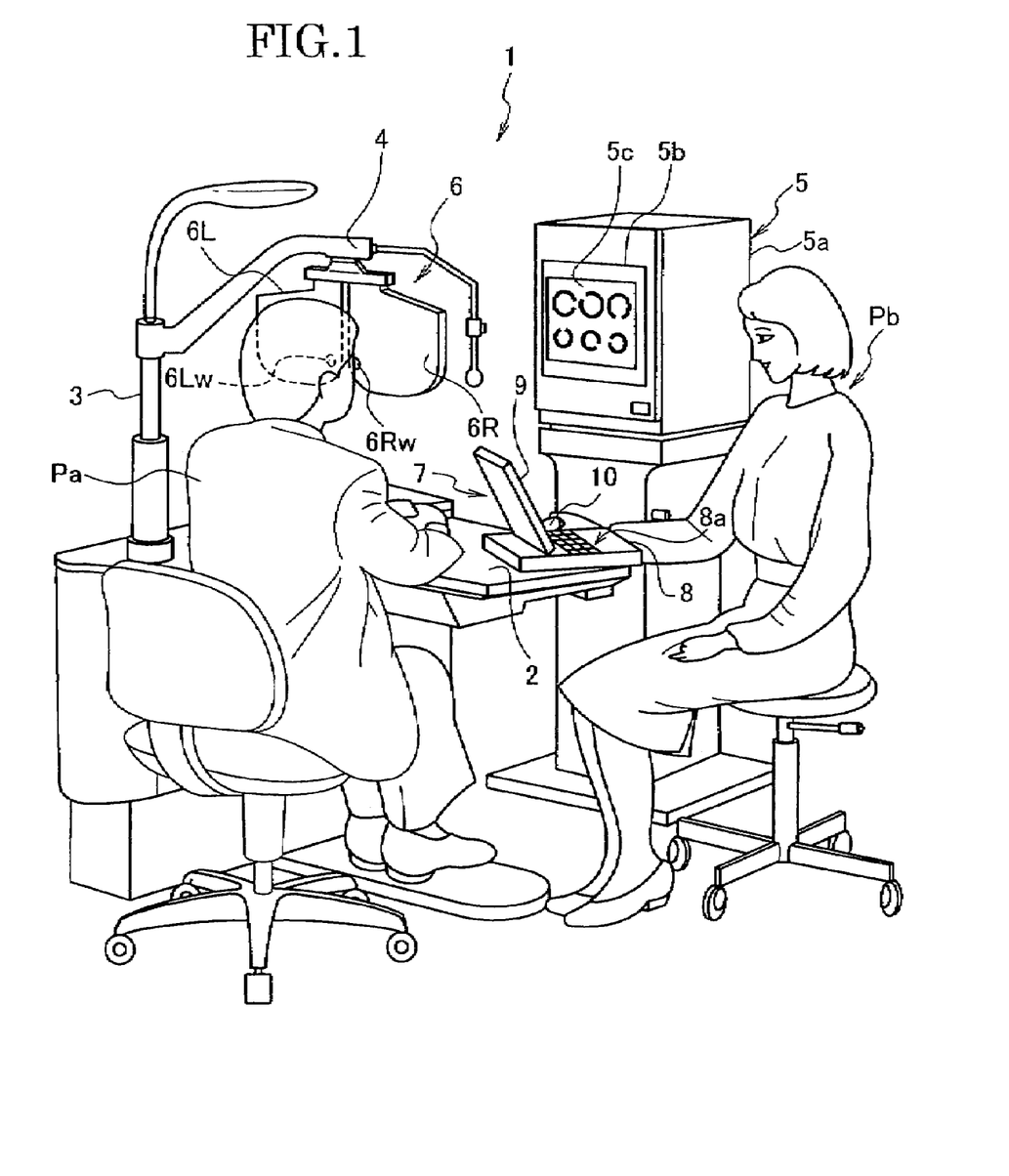
FIG. 1 is a perspective view showing a subjective optometric apparatus including a program for optometry according to an embodiment of the present invention.

In FIG. 1, reference number 1 indicates a subjective optometric apparatus. The subjective optometric apparatus 1 includes a table 2 for optometry, a support 3 provided on a corner of the table 2 so as to be capable of extending in a vertical direction, and a supporting arm 4 mounted on the support 3 so as to be capable of horizontally turning.

The subjective optometric apparatus 1 also includes a target displaying apparatus 5 disposed with an interval from the table 2, a phoroptor 6 supported on the supporting arm 4, and a controller 7 mounted on the table 2.

The target displaying apparatus 5 is provided with a plurality of optometric charts (not shown), a driving motor (driving device) such as a pulse motor driving the plurality of optometric charts, and a drive control device which drives to control the driving motor and selectively displays one of the plurality of optometric charts. In addition, the target displaying apparatus 5 has at a front thereof a main body 5a, provided with a display window 5b. A selected chart 5c is displayed on the display window 5b. For the target displaying apparatus 5, since conventionally known structures disclosed, for example, in Japanese Patent Application Publication No. 2002-143092 can be adopted, detailed descriptions are omitted. In addition, the plurality of optometric charts may be selectively displayed on a display device (display device) such as a liquid crystal display (LCD).

Furthermore, the phoroptor 6 is provided with optometric units 6L, 6R, which are disposed symmetrically to each other and the optometric units 6L, 6R have optometric windows 6Lw, 6Rw, respectively. The optometric unit 6L includes a plurality of test lenses. Each of the plurality of test lenses has a different refractive power (condition of refraction) from each other. The optometric unit 6L also includes a driving motor (driving device, not shown) such as a pulse motor driving the plurality of test lenses, and a drive control device (not shown) which drives to control the driving motor such that one of the optical devices such as the plurality of test lenses, polarizing plates and dousers is set on the optometric window 6Lw.

In addition, the optometric unit 6R is structured in the same way as the optometric unit 6L. For the phoroptor 6 having the above-mentioned optometric units 6L, 6R, since conventionally known structures disclosed, for example, in Japanese Patent Application Publication No. 2002-143092 can be adopted, detailed descriptions are omitted.

An examinee Pa can visibly recognize the chart 5c of the target displaying apparatus 5 via the optometric windows 6Lw, 6Rw. In addition, an examiner Pb operates the target displaying apparatus 5 and the phoroptor 6 by using the controller 7.

The controller 7 includes an operating panel 8 to execute settings of various tests, an LCD device (display device) 9 for a monitor displaying refractive power data, and a mouse 10 used for operations of changing data displayed on the LCD device 9 and switching displays.

Figure 2:
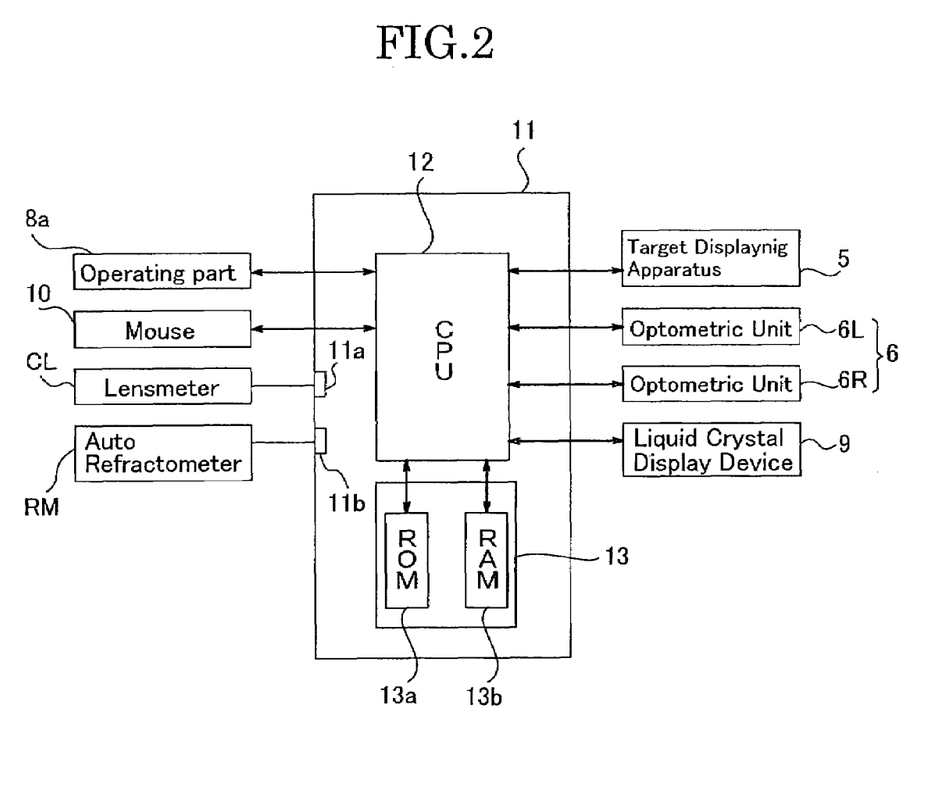
FIG. 2 is a schematic diagram controlling the subjective optometric apparatus illustrated in FIG. 1.

A control device 11 shown in FIG. 2 is provided in the operating panel 8, and an operating part 8a (a detailed illustration thereof is omitted) is provided on an upper surface of the operating panel 8. The control device includes a CPU (processing device) 12 and a memory 13 (storing device as recording device) connected to the CPU. The memory 13 includes a ROM 13a and a RAM 13b. A program for optometry (an examination program) having a first unit to measure an amount of heterophoria of the eyes of an examinee in a horizontal heterophoria examination, a second unit to display an operating method to allow the examinee to implement a Sheard criterion identifying examination on a display device, a third unit to allow the examinee to implement a convergent or divergent test of the eyes based on the operating method, and a fourth unit to calculate a prism amount for prescriptions based on the heterophoria amount and the convergence or divergence of the eyes, is stored in the ROM 13a. The optometric program has also a display window setting device (a part of the program) to set a window, which is selected from a plurality of reference windows to display start data.

Furthermore, in the present embodiment, objective data are maintained to be non-erasable during a subjective examination and used as initial data.

The CPU 12 is connected to the drive control device (not shown) of the target displaying device 5 and the drive control device (not shown) of the phoroptor 6. Moreover, the LCD device 9 and the mouse 10 are connected to the CPU 12.

The control device 11 is provided with data input parts 11a, 11b. Input to the data input part 11a are objective refractive power data from an auto refractometer RM as an objective optometric apparatus, and input to the data input part 11b are lens refracting strength data from a lensmeter CL.

Figure 3:
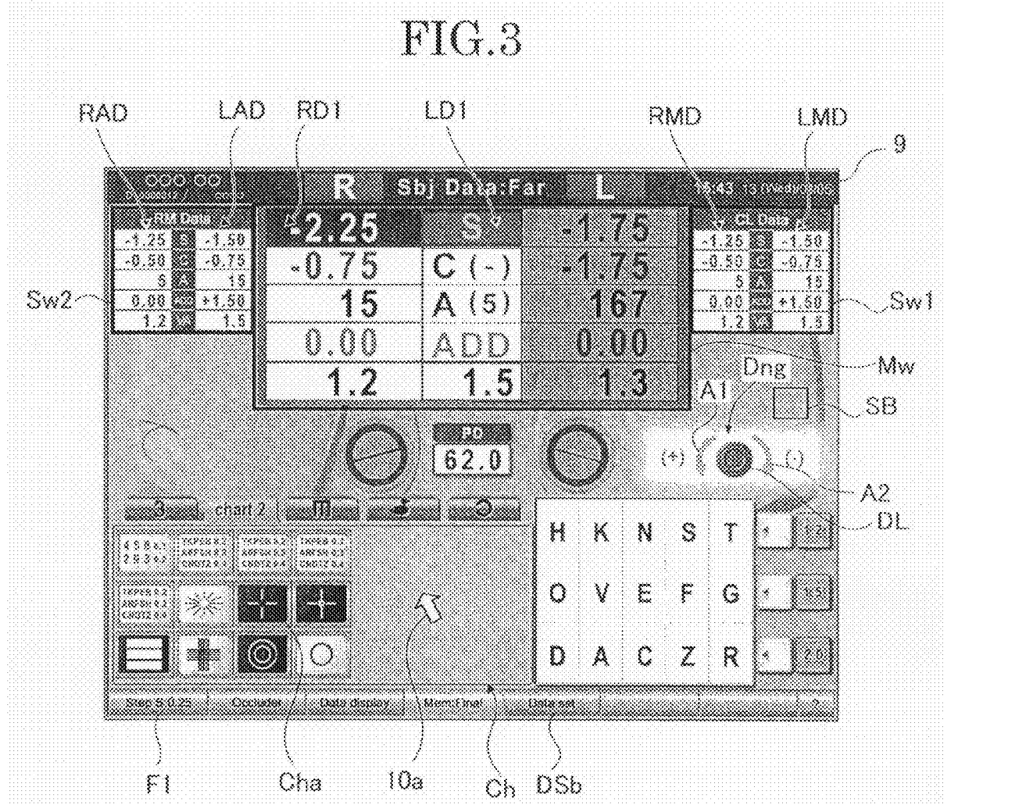
FIG. 3 is an explanatory view illustrating an example of a data display image displayed on a liquid crystal display (LCD) device shown in FIG. 1.

The CPU 12 allows a main window Mw (a main refractive power data window) to be displayed as a main data displaying window on an upper portion of a center of a horizontal line of the LCD device 9 as shown in FIG. 3. The CPU 12 also allows reference windows Sw1, Sw2 (reference refractive power data windows) to be displayed as reference data displaying windows on both sides of the main window Mw.

The refractive power data of the main window Mw may be configured to be automatically interchanged with any of the refractive power data of the reference windows Sw1, Sw2 when a cursor 10a of the mouse 10 is moved to a data switching button Dsb "Data set" of the LCD device 9 and a left button (not shown) of the mouse 10 is clicked. In the present embodiment, the refractive power data of the main window Mw are configured to be automatically interchanged with the refractive power data of the reference window Sw1.

The CPU 12 is configured to allow the main data to be displayed on the main window Mw, the first reference data to be displayed on the reference window Sw1 (that is, the first reference window), and the second reference data to be displayed on the reference window Sw2 (that is, the second reference window).

In the present embodiment, lens refractive power data (CL Data) of glasses measured, for example, by a lensmeter as the first reference data (an outside refractive power data) are displayed on the reference window Sw1. Subjective optometric data (RM Data) measured, for example, by an auto refractometer as the second reference data (an outside refractive power data) are displayed on the reference window Sw2.

In addition, the CPU 12 drives to control the drive control device (not shown) of each of the optometric units 6R, 6L based on the main data displayed on the main window Mw to allow the test lens to be disposed on the optometric windows 6Rw, 6Lw of the optometric units 6R, 6L. Thereby, a dioptric power of the test lens set on each of the optometric windows 6Rw, 6Lw corresponds to a dioptric power set with the main data. The main data can be changed by an operation of the operating panel 8. Since conventionally known structures can be adopted for the structure, detailed descriptions are omitted.

Moreover, a spherical diopter power S, a cylindrical diopter power C, a cylinder axis angle A, and an addition power ADD of the refractive power data are displayed on a center of a horizontal line of the main window Mw. Refractive power data RD1, LD1 of the test lenses (not shown) which are set on the optometric windows 6Rw, 6Lw of the optometric units 6R, 6L, as the first reference data, respectively, are displayed on right and left sides of the S, C, A and ADD displayed on the main window Mw, respectively.

Moreover, a spherical diopter power S, a cylindrical diopter power C, a cylinder axis angle A, an addition power ADD, and a visual acuity VA of the refractive power data are displayed on a center of a horizontal line of the reference window Sw1. Displayed on right and left sides of the S, C, A, ADD and VA displayed on the reference window Sw1 are lens refractive power data RMD [first reference data (right)], which corresponds to a dioptric power of a right lens of glasses worn by the examinee and lens refractive power data LMD [first reference data (left)], which corresponds to a lens dioptric power of a left side of the glasses, respectively.

Furthermore, a spherical diopter power S, a cylindrical diopter power C, a cylinder axis angle A, an addition power ADD, and a visual acuity VA of the refractive power data are displayed on a center of a horizontal line of the reference window Sw2. Right objective refractive power data RAD [second reference data (right)] and left objective refractive power data LAD [second reference data (left)] of the examinee are displayed on right and left sides of the S, C, A, ADD and VA displayed on the reference window Sw2, respectively.

On the other hand, as shown in FIG. 3, the CPU 12 is configured to allow the windows Mw, Sw1 and Sw2 to be displayed on the LCD device 9 during a subjective examination for distance and a navigation image Dng (a dial navigation), which shows a direction of a turning operation of a dial (not shown) of the operating panel 8 to be displayed on a lower part of the reference window Sw1.

In FIG. 3, the navigation image Dng includes a dial image DL corresponding to a dial (not shown) of the operating panel 8, arrows A1, A2 showing a turning direction of the dial (not shown), (+) shown on a left of the arrow A1, and (−) shown on a right of the arrow A2.

In addition, the arrows corresponding to each of (+), (−) show increasing and decreasing directions of the lens refracting strength of the test lens disposed on the optometric windows 6Lw, 6Rw, respectively. Based on the display, a turning operation of the dial (not shown) of the operating panel 8 according to the displayed arrows A1, A2 of the dial image DL allows the data displayed on the main window Mw, such as S, C, or the like, to increase or decrease.

Moreover, depending on contents of the examination, the way the examinee views the chart and in which direction the dial is required to be turned are displayed in relation to a combination of the used charts and the examined test.

For example, a chart displaying part Ch is displayed on a lower left-hand side of the LCD device 9 by the CPU 12. When the left button (not shown) of the mouse 10 is clicked after a cross chart button Cha for a heterophoria examination displayed on the chart displaying part Ch is selected using the cursor 10a of the mouse 10, the CPU 12 allows a cross chart button Cha1 for the heterophoria examination shown in FIG. 4 to be displayed on the display window 5b of the target displaying apparatus 5. In this case, the CPU 12 allows a navigation image Dng' shown in FIG. 5 to be displayed in place of the navigation image Dng on the LCD device 9.

Figure 4:
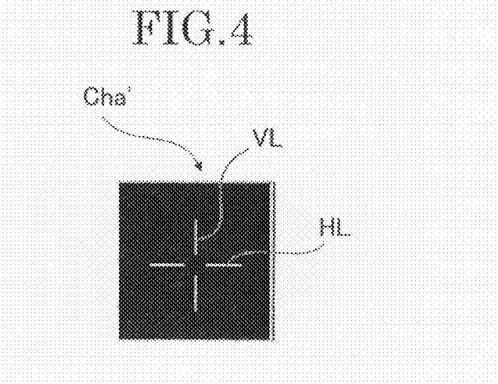
FIG. 4 is an explanatory view illustrating a cross chart displayed on a target displaying apparatus shown in FIG. 1.

Polarizing films are applied along a line VL and a line HL which are shown in the chart of FIG. 4 and are at right angles to each other. The examinee Pa, for example, looks at the chart through a polarizing plate (not shown) parallel to the vertical line with the right eye, and a polarizing plate (not shown) parallel to the horizontal line with the left eye. In this case, the polarizing plate (not shown) parallel to the vertical line and the polarizing plate (not shown) parallel to the horizontal line to allow a vertical line to be visible for the right eye and a horizontal line to be visible for the left eye are disposed on the display windows 6Lw, 6Rw of the optometric units 6L, 6R by the CPU 12.

When the horizontal heterophoria of the examinee Pa is measured, if esophoria exists, the examinee recognizes that the vertical line deviates leftwards and the horizontal line deviates rightwards. On the other hand, if exophoria exists, the examinee recognizes that the vertical line deviates leftwards and the horizontal line deviates rightwards.

Figure 5:
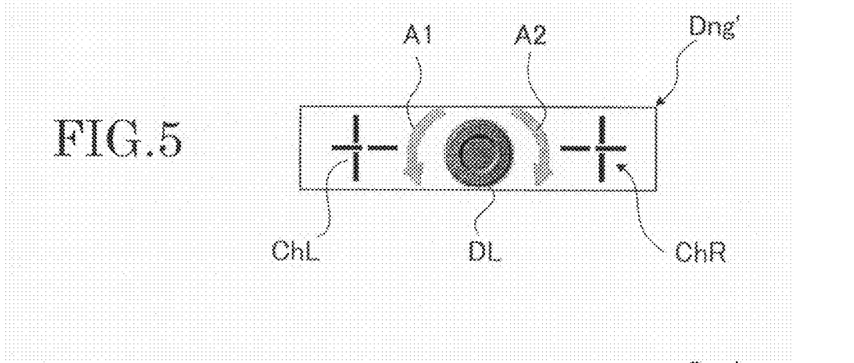
FIG. 5 is an explanatory view illustrating a navigation image displayed on the LCD device during a heterophoria examination.

Furthermore, the navigation image Dng' includes the dial image DL corresponding to the dial (not shown) of the operating panel 8, the arrows A1, A2 showing the turning direction of the dial (not shown), a left chart image ChL to identify a deviation displayed on a left of the arrow A1, and a right chart image ChR to identify a deviation displayed on a right of the arrow A2.

When the above-mentioned horizontal heterophoria examination as a heterophoria examination (a heterophoria test) is completed, the CPU 12 allows a button SB to identify the Sheard criterion to be displayed on the LCD device 9. When the left button (not shown) of the mouse 10 is clicked after the button SB is selected by the cursor 10a of the mouse 10, the CPU 12 allows a navigation image Dng" shown in FIG. 8 to be displayed. The navigation image Dng" includes the dial image DL corresponding to the dial (not shown) of the operating panel 8, the arrows A1, A2 showing a turning direction of the dial (not shown), and a confirmation indication Chp, that is "add up to 8Δ" of a prism amount to confirm the Sheard criterion.

[Operation]

Next, operation of the subjective optometric apparatus configured as mentioned above will be described.

When the apparatus is activated, the CPU 12 loads the program stored in the ROM 13a and sets it in a predetermined memory part of the RAM 13b to operate a display for the optometry on the LCD device 9 by the optometric program as shown in FIG. 3.

In the RAM 13b of the control device 11, the objective refractive power data from an auto refractometer as the objective optometric apparatus are input via the data input part 11a, and the lens refracting strength data from the lensmeter CL are input via the data input part 11b. As shown in FIG. 3, the lens refractive power (lens refracting strength) data are displayed on the reference window Sw1, and the objective data (objective refractive power data) are displayed on the reference window Sw2.

In the present embodiment, the objective data are maintained to be non-erasable during the subjective examination and used as initial data.

Therefore, the CPU 12 of the control device 11 allows the objective data displayed on the reference window Sw2 to be automatically loaded to be displayed on the main data window when the subjective examination is started. The CPU 12 drives to control the drive control device (not shown) of the optometric units 6R, 6L of the phoroptor 6 based on the objective data to set the test lenses on the optometric windows 6Rw, 6Lw of the optometric units 6R, 6L, respectively.

Thereby, the dioptric powers of the test lenses set on the optometric windows 6Rw, 6Lw correspond to the dioptric powers set on the main window, respectively.

The subjective examination (as a known method described in Japanese Patent Application No. 2002-143092) is performed by using the optometric units 6R, 6L set from the objective data to obtain the subjective refractive power data S, C, A, ADD, and the like as shown in the main data window Mw in FIG. 3

The refractive power data of the main window Mw is automatically interchanged with a refractive power data of the reference windows Sw1, which are set to save the data, Sw2 when the cursor 10a of the mouse 10 is moved to the data switching button Dsb "Data set" of the LCD device 9 and a left button (not shown) of the mouse 10 is clicked. The refractive power data saved on the reference window Sw1 may be used as a prescription value for prescriptions to make glasses.

(Heterophoria Test)

The heterophoria test is configured to allow the cross chart button Ch1 of the char displaying part Ch to be selected by the cursor 10a of the mouse 10 and the left button (not shown) of the mouse 10 to be clicked. Thereby, the cross chart Cha' for the heterophoria test shown in FIG. 4 is displayed on the display window 5b of the target displaying apparatus 5 by the CPU 12. In this case, the CPU 12 allows the polarizing plate (not shown) parallel to the vertical line (not shown) and the polarizing plate (not shown) parallel to the horizontal line to be disposed on the optometric windows 6Lw, 6Rw of the optometric units 6L, 6R so that the vertical line is recognized by the right eye and the horizontal line is recognized by the left eye. On the other hand, the CPU 12 allows the navigation image Dng' shown in FIG. 5 to be interchanged with the navigation image Dng to display the navigation image Dng' when the cross chart button Cha is selected and clicked.

Figure 6:
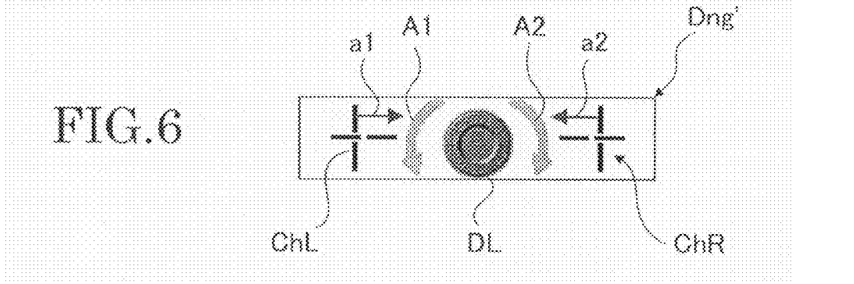
FIG. 6 is an explanatory view illustrating another example of a navigation image displayed on the LCD device during a heterophoria examination.
Figure 9:
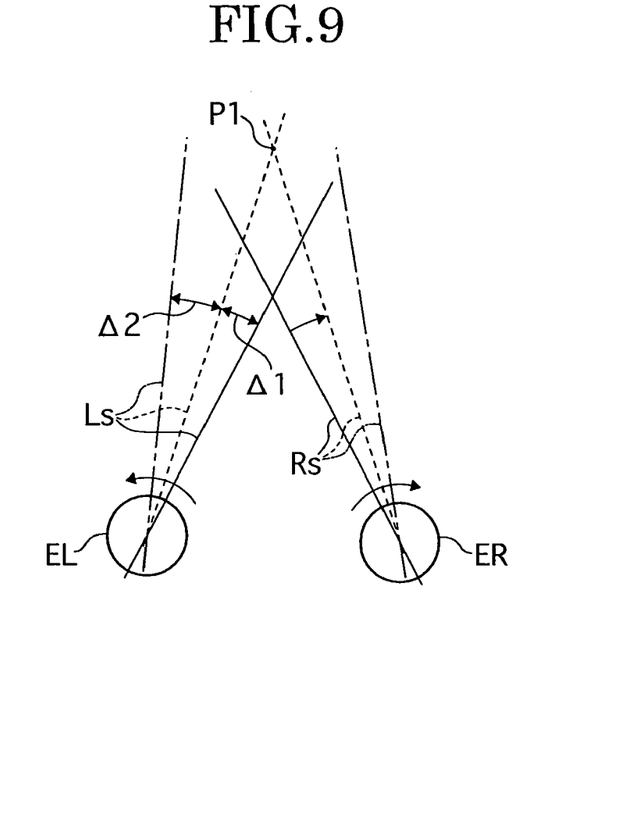
FIG. 9 is a schematically explanatory view illustrating esophoria and exophoria.

As mentioned above, when the horizontal heterophoria of the examinee Pa is measured based on the chart, if esophoria exists, eyes to be examined EL, ER recognize that the vertical line deviates rightwards and the horizontal line deviates leftwards, as shown by the right chart image ChR in FIGS. 5 and 6. In addition, for example, the cross chart Cha' is displayed at a point of an objective point P1 shown in FIG. 9 as an object displayed on the window 5b of the target displaying apparatus 5. If heterophoria does not exist in a normal case, lines of sight Ls, Rs of the eyes EL, ER pass through the objective point Pa as shown by dotted lines in FIG. 9. However, if esophoria exists, for example, the lines of sight Ls, Rs of the eyes deviate toward positions shown by solid lines which are positioned at inner sides of the dotted lines and do not pass through the objective point P1.

Moreover, if exophoria exists, the examinee recognizes that the vertical line deviates leftwards and the horizontal line deviates rightwards, as shown by the left chart image ChL in FIGS. 5 and 6. In addition, in the case that exophoria exists, for example, the lines of sight Ls, Rs of the eyes EL, ER deviate toward positions shown by chain lines which are positioned at outer sides of the dotted lines and do not pass through the objective point P1.

Figure 10:
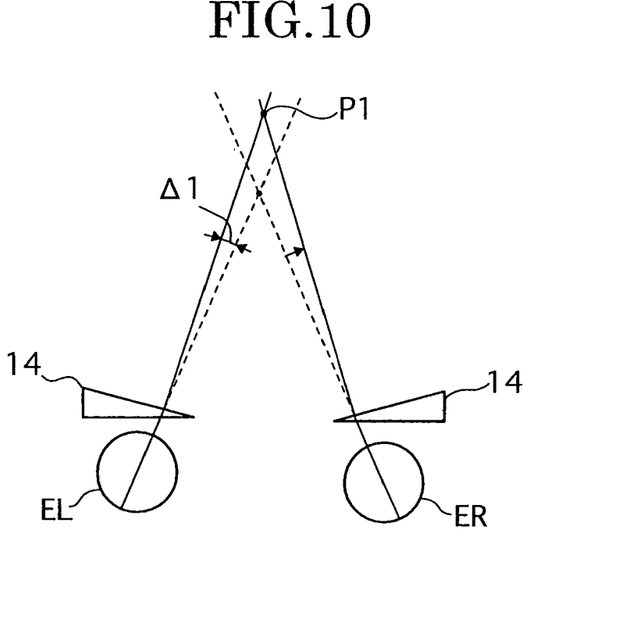
FIG. 10 is a schematic explanatory view illustrating correction of esophoria.
Figure 11:
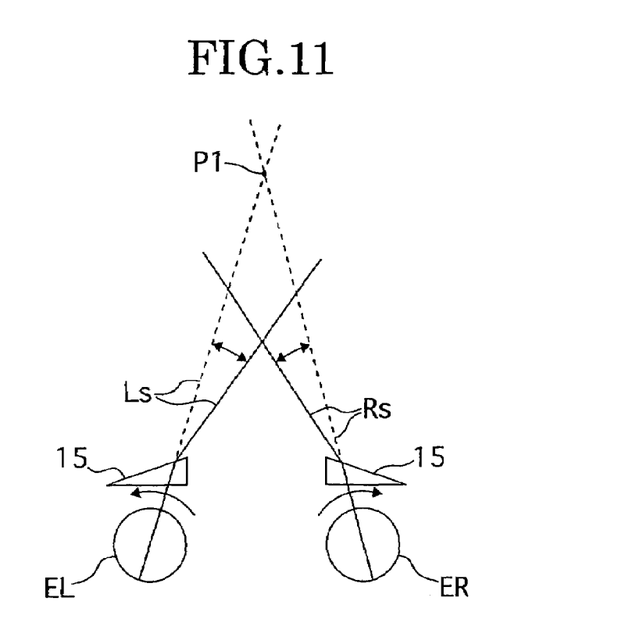
FIG. 11 is a schematic explanatory view illustrating correction of exophoria.

During the above-mentioned heterophoria test (the heterophoria examination), a BO prism (Base-Out prism) 14 may be added for a correction of the esophoria shown in FIG. 10, and a BI prism (Base-In prism) 15 may be added for a correction of the exophoria shown in FIG. 11. For the correction of the esophoria, a prism amount may be set such that the lines of sight Ls, Rs of the eyes EL, ER are changed from the position shown by the dotted lines to the solid lines by the BO prism 14 as shown in FIG. 10 to pass through the objective point. In addition, for the correction of the exophoria, the prism amount may be set such that the lines of sight Ls, Rs of the eyes EL, ER pass through the objective point P1 as shown by the dotted lines by the BI prism 15 as shown in FIG. 11 to pass through the objective point.

The prisms 14, 15 are provided on the optometric windows 6Lw, 6Rw so as to be capable of adjusting the prism amounts. The dial (not shown) of the operating panel 8 is turned in the same direction as the arrows A1 or A2 of the navigation image Dng' so that the prism amounts are adjusted. Thereby, the prism amounts of the prism 14, 15 may be changed stepwisely or continuously. The prism amounts are displayed on the main window Mw. Since for the configuration for changing the prism amounts, conventionally known structures can be adopted, detailed descriptions are omitted.

Accordingly, the examiner is notified that he need only ask, for example, "which side of the horizontal line is the vertical line?" while watching the right chart image ChL, ChR shown in FIGS. 5, 6 during the heterophoria test. At the same time, the examiner is also notified that he need only turn the dial (not shown) to the right (in the arrow A2 direction) when the vertical line deviates rightwards, and turn the dial (not shown) to the left (in the arrow A1 direction) when the vertical line deviates leftwards.

Furthermore, in order to clarify the turning direction of the dial (not shown), arrows a1, a2 showing a direction in which the vertical line moves during the turning of the dial are displayed on the LCD device 9.

Figure 7:
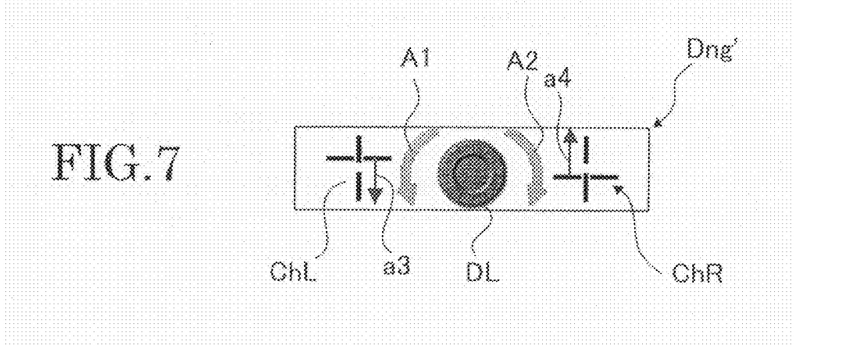
FIG. 7 is an explanatory view illustrating another example of a navigation image displayed on the LCD device during a heterophoria examination.

On the other hand, vertical heterophoria may be measured. The eyes EL, ER recognize that the horizontal line deviates upwardly with respect to the vertical line if a right and upper heterophoria exists, and that the horizontal line deviates downwardly with respect to the vertical line if a left and upper heterophoria exists, as shown by the right chart image ChR in FIG. 7. In this case, arrows a3, a4 showing a direction in which the horizontal line moves may be displayed as well as the arrows a1, a2.

(Calculation of Sheard Criterion Value)

After the above-mentioned horizontal heterophoria test (the horizontal heterophoria examination) is completed, a Sheard criterion identifying test is performed by a Sheard criterion identifying unit. The Sheard criterion identifying unit may include for example, the optometric program stored in the ROM 13a, the CPU 12, the operating part 8a, and the LCD device 9. The CPU 12 allows the button SB to identify the Sheard criterion to be displayed on the LCD device 9, as shown in FIG. 3.

In this case, data of the prism amount displayed on the main window Mw are automatically interchanged with the refractive power data of the reference window Sw1, which are set to save the data as the heterophoria amount when the cursor 10a of the mouse 10 is moved to the data switching button Dsb "Data set" of the LCD device 9 and the left button (not shown) of the mouse 10 is clicked. The prism amount data saved on the reference window Sw1 may be used as a prescription value for divergence power tests or making glasses.

Figure 8:
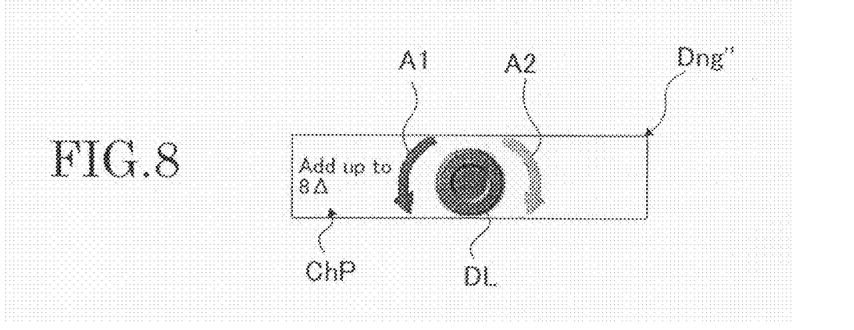
FIG. 8 is an explanatory view illustrating an example of a navigation image displayed on the LCD device during a fusional convergence reserve or a fusional divergence reserve examination.

When the examiner selects the button SB using the cursor 10a of the mouse 10 and clicks the left button (not shown) of the mouse 10, the CPU 12 allows the navigation image Dng" to be displayed as shown in FIG. 8 in the case of esophoria. In the navigation image Dng", the confirmation indication Chp, that is "add up to 8Δ" of the prism amount to confirm the Sheard criterion is displayed on the left side of the arrow A1. Thereby, the examiner is notified on the navigation image Dng" to turn the dial (not shown) of the operating panel 8 in the arrow A1 direction until the prism amount reaches 8 prisms in the divergence test for esophoria.

In addition, instead of the button SB displayed as a software image, the button (not shown) of the operating panel 8 may be used as a trigger to display the navigation image Dng". For example, in the optometric program which programs an order of various processes for the optometry, since the test is progressed to a next process generally by using the button provided on the operating panel 8 of the controller 7, the button for progressing to a next process may be pushed to allow the Sheard criterion identifying test to be automatically performed after the horizontal heterophoria examination.

When the Sheard criterion identifying test is performed, a formula for calculating the Sheard criterion value based on the pre-input heterophoria amount is used so that a reference value corresponding to "a limit value of a fusional convergence reserve in a case that the examinee has exophoria or a fusional divergence reserve in a case that the examinee has esophoria to judge whether the prism prescription is not required" is automatically calculated and exhibited to the examiner.

Figure 12:
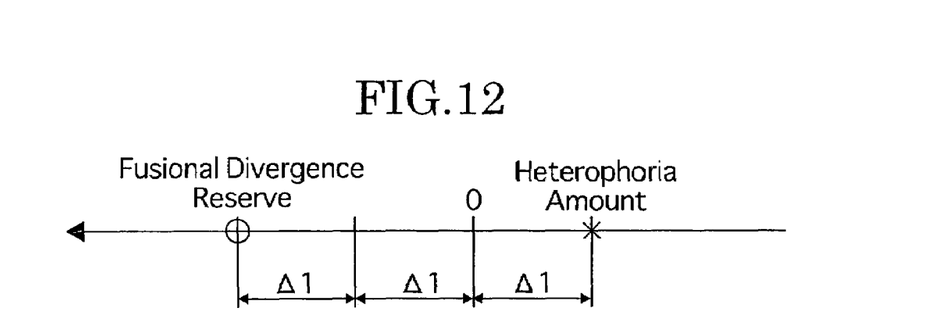
FIG. 12 is an explanatory view showing a fusional divergence reserve.
Figure 13:
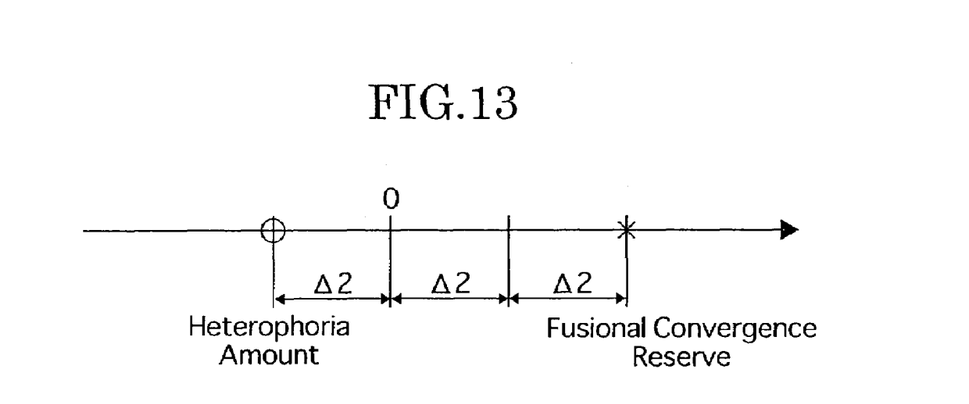
FIG. 13 is an explanatory view showing a fusional convergence reserve.

For example, in the case of esophoria, when the heterophoria amount is Δ1 as shown in FIG. 12, the fusional divergence reserve is twice Δ1 and in the case of exophoria, when the heterophoria amount is Δ2 as shown in FIG. 13, the fusional convergence reserve is twice Δ2. Accordingly, the Sheard criterion value is calculated based on a formula as follows.

$$Sh = H \times 2 \quad (1)$$

where Sh is a Sheard criterion value and H is a heterophoria amount (amount of esophoria or exophoria).

Practically, the CPU 12 calculates the Sheard criterion value by using the formula (1) based on the heterophoria amount (the prism amount) obtained from the above-mentioned heterophoria test.

For displaying a guidance to operate the dial (not shown) for calculating the Sheard criterion value, in a case of a software where a correcting value is changed by using, for example, a dial controller, the turning direction of the dial and the reference value may preferably be displayed on the navigation image Dng", as mentioned above.

Moreover, for displaying the guidance to operate the dial (not shown), preferably messages may be displayed such that Help is displayed on the software image by the optometric program, a message box, or the like, that is to say, for example, "add the Base-In prism and confirm whether the fusional divergence reserve is 8 prism (8Δ) or more" may be displayed.

An amount of convergence or divergence of the eyes is obtained by a convergence or divergence amount detecting unit. The convergence or divergence amount detecting unit may include as described below. That is, the examiner performs the test according to the above-mentioned guidance. In order to calculate an optimum prism correcting value, the software (the optometric program) is required to receive a result of the fusional convergence reserve or the fusional divergence reserve. Therefore, an input device such as a button is provided and the examiner is notified by the Help or the message box on the software image to allow the button to be pushed when the fusional convergence reserve or the fusional divergence reserve are measured.

In addition, if the Sheard criterion provided from the formula (1) is satisfied (if the fusional convergence reserve or the fusional divergence reserve is the Sheard criterion value or more), basically a prism prescription is not necessary, that is, it is not necessary to continue measurements for identifying the Sheard criterion.

Accordingly, after an upper limit value for the measurements is provided based on the reference value, a message, for example, "no more confirmation is necessary" may be displayed in a case in which the value reaches or exceeds the limit value to allow extra confirmations to be preliminarily avoided.

When the measurement of the fusional convergence reserve or the fusional divergence reserve is completed and then the button is pressed for inputting results, the prism amount which is needed for the examinee is calculated based on the results.

If the input value is the reference value obtained from the formula (1) or more, the examiner is notified that no prism prescriptions are required.

On the other hand, if the input value does not satisfy the criterion obtained from the formula (1) (that is, less than the reference value), a required prism prescription value is calculated. That is, it is only necessary for an adequate correcting value to satisfy the following equation.

$$F \geq H \times 2 \quad (2)$$

where F is a fusional reserve (fusional convergence reserve or fusional divergence reserve).

In this case, the equation (2) is modified and the required prism prescription value is obtained from the following equation (3), that is, the CPU 12 calculates the prism prescription value by the following equation.

$$Pr = (H \times 2 - F)/3 \quad (3)$$

where Pr is a prism prescription value.

For example, if the fusional divergence reserve of the examinee having esophoria of 8Δ (8 prisms) is 13Δ (prism), it is calculated by the formula (2) that the prism prescription value is 1Δ (1 prism). Since the correction is carried out for esophoria, it is calculated that the prism prescription value is 1Δ BO (prism 14 corresponds to 1 prism to correct outwardly).

The manner of notifying the prescription value calculated by the CPU 12 is comprised of a combination of directly inputting the prism correcting value to a data input area, displaying the image, voice information, and the like. Alternatively, besides the prism correcting value, an area is provided for showing the prism correcting value satisfying the Sheard criterion to display the prescription value. Moreover, the above-mentioned optometric program may be recorded in a recording media such as a magnetic disc, a magnetic optical disc, or a flash memory or other memories to be provided.

As described above, the optometric program according to the embodiment of the present invention operates a computer as a first unit to measure an amount of heterophoria of eyes of an examinee to be examined in a horizontal heterophoria examination, a second unit to display an operating method on a display device to allow the examinee to implement a Sheard criterion identifying test, a third unit to allow the examinee to implement a convergent or divergent test of the eyes based on the operating method, and a fourth unit to calculate a prism amount for prescriptions based on the heterophoria amount and the convergence or divergence of the eyes.

This optometric program is provided with a function for performing the Sheard criterion identifying examination in a guidance system seamlessly after the heterophoria examination. Therefore, the examiner is not required to have detailed knowledge of the Sheard criterion. In addition, if the convergence amount or the divergence amount of the examinee does not satisfy the criterion, by provision of a function for calculating a suitable prism prescription value based on the Sheard criterion value, an optimum prism prescription may be determined.

Furthermore, the optometric program of the embodiments of the present invention has a function for calculating a required value of the fusional convergence reserve or the fusional divergence reserve based on the measured heterophoria amount of the examinee when the Sheard criterion identifying examination is performed, displaying the value, and guiding how to proceed with the optometric examination.

According to this configuration, by following the guide (guidance), the test of the fusional convergence reserve and the fusional divergence reserve may be easily and reliably performed.

Moreover, the optometric program according to the embodiments of the present invention has a function for setting the limit value to be measured based on the calculated value of the fusional convergence reserve or the fusional divergence reserve to control or inform so as not to measure in the case in which the value is the limit value or more.

According to this structure, only by performing the required measurements, an optimum prism prescription can be determined.

Furthermore, the optometric program according to the embodiments of the present invention has a function for calculating the prism prescription value required by the examinee based on the measured value of the fusional convergence reserve or the fusional divergence reserve, displaying to the examiner and inputting automatically the prism prescription value. According to this structure, the optimum prism prescription can be easily and rapidly achieved.

In addition, the recording medium according to the embodiments of the present invention has the above-mentioned optometric program. The subjective optometric apparatus according to the embodiments of the present invention has the above-mentioned optometric program. These recording medium and subjective optometric apparatus provide the advantages concerning the optometric program.

Although the preferred embodiments of the present invention have been described, it should be noted that the present invention is not limited to these embodiments, and various modifications and changes can be made to the embodiments.

What is claimed is:

1. A recording medium having a program for optometry, which is used for a control device, the program comprising:
   a first unit to measure an amount of heterophoria of eyes of an examinee to be examined and determine whether exophoria or esophoria exists in a horizontal heterophoria examination;
   a second unit to calculate a Sheard criterion value based on the measured amount of heterophoria of the eyes of the examinee and cause the display of an operating method to allow the examinee to implement a Sheard criterion identifying examination by use of the calculated Sheard criterion value on a display device;
   a third unit to allow the examinee
      to implement a convergent test of the eyes without implementing a divergent test of the eyes in a case where the exophoria exists and to implement a divergent test of the eyes without implementing a convergent test of the eyes in a case where the esophoria exists based on the operating method, and
      to complete the convergent or divergent test if a fusional convergence or divergence reserve of the eyes satisfies a Sheard criterion based on the Sheard criterion value and to measure the fusional convergence or divergence reserve of the eyes if the fusional convergence or divergence reserve of the eyes does not satisfy the Sheard criterion based on the Sheard criterion value; and
   a fourth unit to calculate a prism amount for prescriptions based on the heterophoria amount and the fusional convergence reserve of the eye in the case where the exophoria exists or the fusional divergence reserve of the eyes in the case where the esophoria exists, if the fusional convergence or divergence reserve of the eyes does not satisfy the Sheard criterion.

2. The recording medium according to claim 1, wherein the control device is configured to
   display the calculated Sheard criterion value; and
   guide how to proceed with an optometric examination.

3. The recording medium according to claim 2, wherein
   the Sheard criterion value is a limit value of the fusional convergence reserve in the case where the exophoria exists or the fusional divergence reserve in the case where the esophoria exists to judge whether the prism prescription is not required; and
   the third unit is configured to judge that the fusional convergence or divergence reserve of the eyes satisfies the Sheard criterion when the fusional convergence or divergence reserve of the eyes is the limit value or more.

4. The recording medium according to claim 3, wherein the control device is configured to
   calculate a prism prescription value required by the examinee based on the measured value of the fusional convergence reserve or the fusional divergence reserve; and
   display to an examiner or input automatically the prism prescription value.

5. A subjective optometric apparatus, having the recording medium according to claim 1.

6. A subjective optometric apparatus, having the recording medium according to claim 2.

7. A subjective optometric apparatus, having the recording medium according to claim 3.

8. A subjective optometric apparatus, having the recording medium according to claim 4.

9. An optometric method, comprising the steps of
   measuring an amount of heterophoria of eyes of an examinee to be examined and determining whether esophoria or exophoria exists in a horizontal heterophoria examination;
   calculating a Sheard criterion value based on the measured amount of heterophoria of the eyes of the examinee;
   displaying an operating method to allow the examinee to implement a Sheard criterion identifying examination on a display device by use of the calculated Sheard criterion value;
   allowing the examinee
      to implement a convergent test of the eyes without implementing a divergent test of the eyes in a case where the exophoria exists and to implement a divergent test of the eyes without implementing a convergent test in a case where the esophoria exists based on the operating method, and
      to complete the convergent or divergent test if a fusional convergence or divergence reserve of the eyes satisfies a Sheard criterion based on the Sheard criterion value and to measure the fusional convergence or divergence reserve of the eyes if the fusional convergence or divergence reserve of the eyes does not satisfy the Sheard criterion based on the Sheard criterion value; and calculating a prism amount for prescriptions based on the heterophoria amount and the fusional convergence reserve of the eyes in the case where the exophoria exists or the fusional divergence reserve of the eyes in the case where the esophoria exists, if the fusional convergence or divergence reserve of the eyes does not satisfy the Sheard criterion.

10. An optometric apparatus, comprising
a heterophoria examination device configured to measure an amount of heterophoria of eyes of an examinee to be examined and determine whether exophoria or esophoria exists;
a display device configured to display an operating method to allow the examinee to implement a Sheard criterion identifying examination;
a Sheard criterion identifying device configured to calculate a Sheard criterion value from the measured amount of heterophoria of the eyes;
a divergence or convergence amount examination device configured
   to implement a convergence test of the eyes without implementing a divergent test of the eyes and to implement a divergent test of the eyes without implementing a convergent test in a case where the esophoria exists based on the operating method, and
   to complete the convergence or divergence test if a fusional convergence or divergence reserve of the eyes satisfies a Sheard criterion based on the Sheard criterion value and to measure the fusional convergence or divergence reserve of the eyes if the fusional convergence or divergence reserve does not satisfy the Sheard criterion based on the Sheard criterion value; and a control device configured to calculate a prism amount for prescriptions based on the heterophoria amount and the fusional convergence reserve of the eye in the case where the exophoria exists or the fusional divergence of the eyes reserve of the eyes in the case where the esophoria exists, if the fusional convergence or divergence reserve of the eyes does not satisfy the Sheard criterion.

11. The optometric method according to claim 9, wherein
the Sheard criterion value is a limit value of the fusional convergence reserve in the case where the exophoria exists or the fusional divergence reserve in the case where the esophoria exists to judge whether the prism prescription is not required; and
the optometric method further comprises judging that the fusional convergence or divergence reserve of the eyes satisfies the Sheard criterion when the fusional convergence or divergence reserve of the eyes is the limit value or more.

12. The optometric apparatus according to claim 10, wherein
the Sheard criterion value is a limit value of the fusional convergence reserve in the case where the exophoria exists or the fusional divergence reserve in the case where the esophoria exists to judge whether the prism prescription is not required; and
it is judged that the fusional convergence or divergence reserve of the eyes satisfies the Sheard criterion when the fusional convergence or divergence reserve of the eyes is the limit value or more.

13. The recording medium according to claim 3, wherein the limit value is twice the amount of heterophoria of eyes.

* * * * *